United States Patent
Becker et al.

(10) Patent No.: US 9,017,641 B2
(45) Date of Patent: Apr. 28, 2015

(54) HYDROGEN PURIFICATION PROCESS

(75) Inventors: Christopher L. Becker, Manhattan, KS (US); James R. Lattner, LaPorte, TX (US); Keith H. Kuechler, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/983,974

(22) PCT Filed: Nov. 21, 2011

(86) PCT No.: PCT/US2011/061702
§ 371 (c)(1),
(2), (4) Date: Nov. 21, 2013

(87) PCT Pub. No.: WO2012/115694
PCT Pub. Date: Aug. 30, 2012

(65) Prior Publication Data
US 2014/0314659 A1    Oct. 23, 2014

Related U.S. Application Data (60) Provisional application No. 61/444,882, filed on Feb. 21, 2011.

(30) Foreign Application Priority Data

Apr. 5, 2011  (EP) .................................. 11161113

(51) Int. Cl.
*C01B 3/02* (2006.01)
*C01B 3/22* (2006.01)
(Continued)

(52) U.S. Cl.
CPC ... *C01B 3/22* (2013.01); *C01B 3/52* (2013.01); *B01D 53/1406* (2013.01); *B01D 53/1418* (2013.01); *B01D 53/263* (2013.01); *C07C 37/08* (2013.01)

(58) Field of Classification Search
CPC ......................................................... C01B 3/22
See application file for complete search history.

(56) References Cited

U.S. PATENT DOCUMENTS 2,083,877 A    6/1937    Steck et al.
2,152,163 A *  3/1939    Tulleners ....................... 558/43
(Continued)

FOREIGN PATENT DOCUMENTS

EP    0 293 032    11/1988
EP    0 319 302    6/1989
(Continued)

OTHER PUBLICATIONS

JP 51117995 Translation.*
(Continued)

*Primary Examiner* — Melvin C Mayes
*Assistant Examiner* — Kenneth Vaden (57) ABSTRACT

In a process for purifying a hydrogen stream, the stream is contacted with a first washing fluid in a first purification zone under conditions effective to transfer at least some water from the hydrogen stream to the first washing fluid, thereby transforming the hydrogen stream into a water-depleted hydrogen stream. At least a portion of the water-depleted hydrogen stream may then be transferred from the first purification zone to a second purification zone, where it is contacted with a second washing fluid under conditions effective to transfer at least some oxygenates from the water-depleted hydrogen stream to the second washing fluid.

24 Claims, 2 Drawing Sheets

(51) Int. Cl.
*C01B 3/52* (2006.01)
*B01D 53/14* (2006.01)
*B01D 53/26* (2006.01)
*C07C 37/08* (2006.01)

(56) References Cited

U.S. PATENT DOCUMENTS

| | | | |
|---|---|---|---|
| 3,580,970 A * | 5/1971 | Swift | 568/799 |
| 4,250,118 A | 2/1981 | van de Mond et al. | |
| 4,418,214 A | 11/1983 | Turcotte | |
| 4,439,409 A | 3/1984 | Puppe et al. | |
| 4,826,667 A | 5/1989 | Zones et al. | |
| 4,954,325 A | 9/1990 | Rubin et al. | |
| 5,236,575 A | 8/1993 | Bennett et al. | |
| 5,250,277 A | 10/1993 | Kresge et al. | |
| 5,362,697 A | 11/1994 | Fung et al. | |
| 6,037,513 A | 3/2000 | Chang et al. | |
| 6,049,018 A | 4/2000 | Calabro et al. | |
| 6,077,498 A | 6/2000 | Diaz Cabañas et al. | |
| 6,201,157 B1 | 3/2001 | Keenan | |
| 6,720,462 B2 | 4/2004 | Duda et al. | |
| 6,756,030 B1 | 6/2004 | Jan et al. | |
| 8,487,140 B2 * | 7/2013 | Buchanan et al. | 568/799 |

FOREIGN PATENT DOCUMENTS

| | | |
|---|---|---|
| GB | 939613 | 10/1963 |
| JP | 51117995 | * 10/1976 |
| WO | WO 97/17290 | 5/1997 |
| WO | WO 2007/084440 | 7/2007 |
| WO | WO 2009/025939 | 2/2009 |
| WO | WO 2010/024975 | 3/2010 |

OTHER PUBLICATIONS

Periodic Table of the Elements, Chemical and Engineering News, vol. 63, No. 5, p. 27 (1985).

* cited by examiner

Fig. 1

Fig. 2

HYDROGEN PURIFICATION PROCESS

PRIORITY CLAIM TO RELATED APPLICATIONS

This application is a National Stage Application of International Application No. PCT/US2011/061702 filed Nov. 21, 2011, which claims priority to U.S. Provisional Application Ser. No. 61/444,882 filed Feb. 21, 2011, and European Application No. 11161113.3 filed Apr. 5, 2011, the disclosures of which are fully incorporated herein by their reference.

FIELD

The present invention relates to a process for purifying the hydrogen by-product generated in the dehydrogenation of cyclohexanone to produce phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone.

Another process to produce phenol involves the hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513.

However, one problem in producing phenol by way of the cleavage of cyclohexylbenzene hydroperoxide is that the cyclohexanone and phenol produce an azeotropic mixture composed of 28 wt % cyclohexanone and 72 wt % phenol. Thus any attempt to separate the cleavage effluent by simple distillation results in this azeotropic mixture.

To obviate this problem, International Patent Publication No. WO2010/024975 proposes to integrate the cyclohexylbenzene production, oxidation and cleavage steps with a dehydrogenation step whereby at least a portion of the cyclohexanone is converted to additional phenol and hydrogen. The co-produced hydrogen is then separated from the phenol product and recycled to the benzene hydroalkylation step. It has, however, now been found that the separated hydrogen contains impurities, particularly water and $C_6$ oxygenates, which, if not removed, may be detrimental to the catalyst employed in the benzene hydroalkylation reaction.

According to the present invention, there is provided a process for removing water and organic oxygenate impurities from a hydrogen stream, such as that produced in a cyclohexanone dehydrogenation process, wherein the hydrogen stream is subjected to a series of washing steps. The process provides a simple and effective method of removing the water and organic oxygenate impurities from the hydrogen stream thereby allowing the purified hydrogen to be employed in catalytic processes, such as benzene hydroalkylation.

U.S. Pat. No. 4,250,118 discloses an improved process for the preparation of cyclohexanone from benzene, wherein the benzene is hydrogenated in a gaseous phase in a hydrogenation zone to form cyclohexane; the cyclohexane is oxidized in a liquid phase to form a mixture containing cyclohexanol and cyclohexanone; the cyclohexanone is separated from this mixture and is catalytically dehydrogenated to form cyclohexanone and a hydrogen containing gas; and the resulting hydrogen containing gas is purified in a washing zone by washed with cyclohexane or benzene before the purified hydrogen gas is fed to the hydrogenation zone.

SUMMARY

In one aspect, the invention resides in a process for purifying a hydrogen stream, the process comprising:

(a) contacting the hydrogen stream in a first purification zone with a first washing fluid under conditions effective to transfer at least some of the water from the hydrogen stream to the first washing fluid, thereby transforming the hydrogen stream into a water-depleted hydrogen stream;

wherein the water-depleted hydrogen stream comprises at least one oxygenate;

(b) transferring at least a portion of the water-depleted hydrogen stream from the first purification zone to a second purification zone; and (c) contacting at least a portion of the water-depleted hydrogen stream with a second washing fluid in the second purification zone under conditions effective to transfer at least some of the at least one oxygenate from the water-depleted hydrogen stream to the second washing fluid.

Conveniently, the hydrogen stream flows in a countercurrent manner to the first washing fluid in the first purification zone, and the water-depleted hydrogen stream flows in a countercurrent manner to the second washing fluid in the second purification zone.

Conveniently, the first washing fluid comprises an oxygenate, such as at least one of phenol and cyclohexanone.

Conveniently, the second washing fluid comprises at least one hydrocarbon, such as at least one of benzene and cyclohexane.

In one embodiment, the first and second purification zones are provided in separate sections of a single purification column arranged such that the second washing fluid does not enter the first purification zone.

Conveniently, the process further comprises:

(d) contacting cyclohexanone with a dehydrogenation catalyst under dehydrogenation conditions effective to convert at least a portion of the cyclohexanone into phenol and produce a dehydrogenation effluent comprising phenol, hydrogen and water;

(e) separating the dehydrogenation effluent into at least a phenol-rich stream and a hydrogen-rich stream, wherein the hydrogen-rich stream comprises at least phenol and water impurities; and (f) supplying the hydrogen-rich stream to the contacting (a).

Conveniently, the dehydrogenation conditions include a temperature of about 250° C. to about 500° C.

In one aspect, the invention resides in a process for producing phenol, the process comprising:

(a) reacting benzene and hydrogen in the presence of a hydroalkylation catalyst to form cyclohexylbenzene;

(b) oxidizing at least a portion of the cyclohexylbenzene to form cyclohexylbenzene hydroperoxide;

(c) cleaving at least a portion of the cyclohexylbenzene hydroperoxide to form phenol and cyclohexanone;

(d) dehydrogenating at least a portion of the cyclohexanone in the presence of a dehydrogenation catalyst to form a dehydrogenation effluent comprising phenol, hydrogen and water;

(e) separating the dehydrogenation effluent into at least a phenol-rich stream and a hydrogen-rich stream, wherein the hydrogen-rich stream comprises at least phenol and water;

(f) contacting at least a portion of the hydrogen-rich stream in a first purification zone with a first washing fluid under conditions effective to transfer at least a portion of the water from the hydrogen-rich stream to the first washing fluid, thereby forming a water-depleted hydrogen-rich stream;

(g) transferring at least a portion of the water-depleted hydrogen-rich stream from the first purification zone to a second purification zone; and (h) contacting at least a portion of the water-depleted hydrogen-rich stream with a second washing fluid in the second purification zone under conditions effective to transfer at least a portion of the phenol from the hydrogen-rich stream to the second washing fluid to form an oxygenate-depleted hydrogen stream, wherein the hydrogen stream and the water-depleted hydrogen stream are gases and the first and second washing fluids are liquids.

Conveniently, the hydroalkylation catalyst is bifunctional catalyst comprising a molecular sieve of the MCM-22 family and a hydrogenation metal, such as palladium and/or platinum.

DETAILED DESCRIPTION OF THE EMBODIMENTS

Described herein is a process for purifying a hydrogen stream comprising at least water and $C_6$ oxygenate impurities. In the process, the hydrogen stream is contacted with a first washing fluid in a first purification zone under conditions effective to transfer at least a portion of the water from the hydrogen stream to the first washing fluid. The resultant dehydrated hydrogen stream is then transferred to a second purification zone, where the hydrogen stream is contacted with a second washing fluid under conditions effective to transfer at least a portion of the oxygenate (e.g., $C_6$ oxygenate) from the hydrogen stream to the second washing fluid.

In one practical embodiment, the present process is employed to purify a hydrogen stream produced as a by-product in an integrated process for producing phenol via cyclohexylbenzene. In this process, the benzene is hydroalkylated to produce cyclohexylbenzene, which then undergoes oxidation and cleavage to produce phenol and cyclohexanone. The cyclohexanone is then dehydrogenated to produce additional phenol together with hydrogen which is desirably recycled to the benzene hydroalkylation step. The hydrogen by-product stream is, however, found to contain water and $C_6$ oxygenate impurities which can be detrimental to the catalyst employed in the hydroalkylation step. By subjecting this hydrogen by-product stream to the present purification process the level of water and $C_6$ oxygenate impurities can be reduced to a sufficiently low level to allow the hydrogen to be recycled to the hydroalkylation step substantially without adverse effect on the hydroalkylation catalyst.

The present purification process will now be more particularly described with reference to its application in aforementioned integrated process for producing phenol from benzene.

However, it will be appreciated the process can also be employed to treat water and $C_6$ oxygenate-containing hydrogen streams from other sources.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following reaction:

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:
  molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
  molecular sieves made from a common second degree building block, being a 2-dimensional tiling of such MWW framework topology unit cells, forming a monolayer of one unit cell thickness, preferably one c-unit cell thickness;
  molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
  molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania, as well as ternary compositions, such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,049,018), zeolite Y, and mordenite. The transalkylation reaction is typically conducted under at least a portional liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 to 500 psig (200 to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above. As used herein, "$C_6$" means a molecule containing six carbon atoms.

When a fraction is described as being "rich in" in a specified species (e.g., $C_6$-rich, benzene-rich or hydrogen-rich), it is meant that the wt % of the specified species in that fraction is enriched relative to the feed stream (i.e., the input).

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds, and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa), a weight hourly space velocity of about 0.2 to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N''-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N''-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in PCT Pub. No. WO 2009/025939.

Cyclohexylbenzene Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least a portionially soluble in the cleavage reaction mixture, is stable at a temperature of at least 185° C. and has a lower volatility (higher normal boiling point) than cyclohexylbenzene. Typically, the acid catalyst is also at least a portionially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less, than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Suitable cleavage conditions include a temperature of greater than 50° C. and no greater than 200° C., or at least 55° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, each of which generally comprise about 40 to about 60 wt %, or about 45 to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product is normally neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 to about 500 psig (5 kPa to 3450 kPa, gauge), or about 10 to 200 psig (70 to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which is then treated to convert at least a portion of the cyclohexanone to additional phenol.

Cyclohexanone Dehydrogenation

In order to maximize the production of phenol from the benzene starting material, at least a portion of the cyclohexanone in the cleavage effluent is subjected to dehydrogenation to phenol according to the following reaction:

As stated above, cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. Moreover, although the efficiency of the separation can be enhanced by conducting the distillation under at least a portional vacuum, phenol/cyclohexanone separation remains a costly process. Thus, in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to the dehydrogenation reaction contains less than 50 wt %, for example less than 30 wt %, such as less than 1 wt %, phenol. The separation of phenol is conveniently effected by vacuum and/or extractive distillation. Additional distillation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

The cyclohexanone dehydrogenation is conducted in the presence of a catalyst which conveniently comprises a support, on which is deposited a dehydrogenation component, typically comprising at least one metal component selected from Groups 6 to 10 of the Periodic Table of Elements.

The catalyst support is typically formed of silica, a silicate, an aluminosilicate, carbon, or carbon nanotubes. In one embodiment, the support comprises a crystalline, mesoporous silicate material selected from MCM-41, MCM-48 and MCM-50. In other embodiments, the silica support has a surface area as measured by ASTM D3663 in the range from about 10 $m^2$/gram to about 1000 $m^2$/gram, such as from about 20 $m^2$/gram to about 500 $m^2$/gram, a pore volume in the range of from about 0.2 cc/gram to about 3.0 cc/gram and a median pore diameter in the range from about 10 angstroms to about 2000 angstroms, such as from about 20 angstroms to about 500 angstroms. Such pore volume and median pore diameter values are determined by mercury intrusion porosimetry as described in ASTM D4284. The support may or may not comprise a binder.

Generally, the dehydrogenation component comprises at least one metal component selected from Groups 6 to 10 of the Periodic Table of Elements, such as platinum and palladium. Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

In one embodiment, the catalyst further contains an inorganic base component comprising a metal component selected from an alkali metal, an alkaline earth metal, an alkali metal compound, and an alkaline earth metal compound, especially potassium or a potassium compound. Typically, the inorganic base component is present in an amount between about 0.1 wt % and about 5 wt %, such as between about 0.1 wt % and about 3 wt %, for example between about 0.1 wt % and about 2 wt %, of the catalyst.

The term "metal component" is used herein to include a metal compound that may not be purely the elemental metal, but could, for example, be at least a portionly in another form, such as an oxide, hydride or sulfide form. The weight % (wt %) of the metal component is herein defined as being measured as the metal present based on the total weight of the catalyst composition irrespective of the form in which the metal component is present.

The dehydrogenation catalyst is typically prepared by initially treating the support, such as by impregnation, with a liquid composition comprising the dehydrogenation component or a precursor thereof, the optional inorganic base component and at least one organic dispersant dispersed in a liquid carrier, such as water. The organic dispersant is generally selected from an amino alcohol and an amino acid, and typically comprises arginine. Generally, the organic dispersant is present in the liquid composition in an amount between about 1 and about 20 wt % of the liquid composition.

The support may be treated with the dehydrogenation component and the inorganic base component in any sequence or simultaneously and the organic dispersant may be present when treating with the dehydrogenation component or the inorganic component or both.

After treatment with the liquid composition, the support is dried to remove the liquid carrier and is then heated in an oxidizing atmosphere, such as air, under conditions to decompose substantially all of the organic dispersant. Suitable conditions for removing the dispersant include a temperature of about 100° C. to about 600° C. for a time of about 0.5 to about 50 hours. The catalyst may then be heated in a reducing atmosphere, such as hydrogen, at a temperature of about 50° C. to about 500° C. for a time of about 0.5 to about 10 hours to reduce the dehydrogenation component.

In one embodiment, the dehydrogenation catalyst has an oxygen chemisorption value of greater than about 30%, such as greater than about 40%, for example greater than about 50%, even greater than about 60%, greater than about 70%, or even greater than about 80%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique. Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [11 kPa to 53 kPa]) is measured at 40° C. with $O_2$ as the adsorbent molecule. Extrapolation of the linear portion of this curve to zero pressure gives the total or combined adsorption uptake.

In another embodiment, the catalyst employed in the cyclohexanone dehydrogenation reaction comprises (i) a support; (ii) a dehydrogenation component comprising at least one metal or compound thereof selected from Groups 6 to 10 of the Periodic Table of Elements; and (iii) tin or a tin compound.

The tin or tin compound may be present in an amount of greater than about 0.01 to about 0.25 wt %, or about 0.02 to about 0.25 wt %, or about 0.03 to about 0.25 wt %, or about 0.04 to about 0.20 wt %, or about 0.05 to about 0.20 wt %, or about 0.05 to about 0.15 wt %, 0.07 to about 0.1 wt % of tin based upon the total weight of the catalyst composition, with ranges from any lower limit to any upper limit being contemplated. In other embodiments, the tin or tin compound may be replaced by another metal component selected from Group 14 of the Periodic Table of Elements.

It will be understood that the tin in the catalyst composition may not be purely the elemental metal, but could, for example, be at least partly in another form, such as a salt, oxide, chloride, hydride, sulfide, carbonate, etc. For purposes of this application, the wt % of tin or tin compound in the catalyst composition is calculated based upon the amount of tin used to form the catalyst composition. For purposes of illustration, a catalyst composition made with 1.9 grams of tin chloride salt (1 gram of tin) and 22.29 grams of tetraammine platinum hydroxide solution (4.486 wt % Pt) that is supported on 98 grams of silicon dioxide contains 1 wt % of tin and 1 wt % Pt, based upon total weight of the catalyst composition.

Moreover, for purposes of determining wt % s of various components, only that portion of the support that supports the dehydrogenation component and/or the tin or tin compound shall be considered.

The catalyst support is typically formed of silica, a silicate, an aluminosilicate, carbon (e.g., carbon nanotubes). In one embodiment, the support comprises a crystalline, mesoporous silicate material selected from MCM-41, MCM-48 and MCM-50. In other embodiments, the silica support has a surface area as measured by ASTM D3663 in the range from about 10 m²/gram to about 1000 m²/gram, such as from about 20 m²/gram, to about 500 m²/gram, a pore volume in the range of from about 0.2 cc/gram to about 3.0 cc/gram and a median pore diameter in the range from about 10 angstroms to about 2000 angstroms, such as from about 20 angstroms to about 500 angstroms. Such pore volume and median pore diameter values are determined by mercury intrusion porosimetry as described in ASTM D4284. The support may or may not comprise a binder. Suitable silica supports are described in, for example, PCT Pub. No. WO/2007084440A1 filed on Jan. 12, 2007 and entitled "Silica Carriers" and is hereby incorporated by reference for this purpose.

Generally, the dehydrogenation component comprises at least one metal component selected from Groups 6 to 10 of the Periodic Table of Elements, such as platinum (Pt) and/or palladium (Pd). Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

In one embodiment, the catalyst further contains an inorganic base component comprising a metal component selected from an alkali metal, an alkaline earth metal, an alkali metal compound, and an alkaline earth metal compound, especially potassium or a potassium compound. Typically, the inorganic base component is present in an amount between about 0.1 wt % and about 5 wt %, such as between about 0.1 wt % and about 3 wt %, for example between about 0.1 wt % and about 2 wt %, of the catalyst.

The dehydrogenation catalyst is typically prepared by sequentially or simultaneously treating the support, such as by impregnation, with one or more liquid compositions comprising the dehydrogenation component or a precursor thereof, the tin component or a precursor thereof and/or the optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between about 1 and about 20 wt % of the liquid composition.

In one preferred embodiment, the catalyst is prepared by sequential impregnation with the tin component being applied to the support before the dehydrogenation component.

After treatment with the liquid composition, the support is heated in one or more stages, generally at a temperature of about 100° C. to about 700° C. for a time of about 0.5 to about 50 hours, to effect one or more of (a) removal of the liquid carrier; (b) conversion of a metal component to a catalytically active form; and (c) decompose the organic dispersant. The heating may be conducted in an oxidizing atmosphere, such as air, or under reducing atmosphere conditions, such as hydrogen. After treatment with a liquid composition containing the dehydrogenation component, the support is generally heated at a temperature of about 200° C. to about 500° C., such as about 300° C. to about 450° C., for a time of about 1 to about 10 hours.

Suitable conditions for the dehydrogenation step comprise a temperature of about 250° C. to about 500° C. and/or a pressure of about 0.01 atm to about 20 atm (1 kPa to 2000 kPa), such as a temperature of about 300° C. to about 450° C. and a pressure of about 1 atm to about 3 atm (100 kPa to 300 kPa). To improve catalyst stability and assist in extracting the hydrogen generated in the dehydrogenation reaction, hydrogen may be cofed to the dehydrogenation reaction, typically such that the molar ratio of hydrogen to cyclohexanone in the dehydrogenation feed is about 0:1 to about 4:1.

The reactor configuration used for the dehydrogenation process generally comprises one or more fixed bed reactors containing the dehydrogenation catalyst. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

The effluent from the cyclohexanone dehydrogenation reaction is composed mainly of phenol and hydrogen, together with some benzene and water as by-products. The desired phenol is easily removed from the reaction effluent by distillation. However, the hydrogen stream recovered from the fractionation operation contains various impurities, which limits its utility, especially for recycle to the benzene hydroalkylation step. In particular, the hydrogen stream contains water, typically present in an amount between about 100 ppmw and about 180,000 ppmw of the total hydrogen stream, and $C_6$ oxygenates (molecules at least containing six carbon atoms and an oxygen atom), particularly phenol and cyclohexanone, typically present in an amount between about 100 ppmw and about 50,000 ppmw of the total hydrogen stream. In various embodiments, the hydrogen stream contains at least 2 wt % of hydrogen, or at least 5 wt %, or at least 10 wt %, or at least 20 wt % hydrogen, based upon total weight of the stream.

Thus, in the present process, the hydrogen stream is subjected to a multi-stage purification process, in which the hydrogen stream is initially supplied to a first purification zone where it is contacted with a first washing fluid under conditions effective to transfer at least some of the water from the hydrogen stream to the first washing fluid, thereby transforming the hydrogen stream into a water-depleted hydrogen stream. As used herein, "water-depleted hydrogen stream" means that the stream contains less water than the hydrogen stream.

In various embodiments, water-depleted hydrogen stream comprises one or more oxygenates (e.g., C6 oxygenates). The oxygenate may be supplied to the water-depleted hydrogen stream from one or more of: (i) the hydrogen stream; and (ii) the first washing fluid.

In various embodiments, at least a portion of the water-depleted hydrogen stream may be transferred from the first purification zone to a second purification zone, where it is contacted with a second washing fluid under conditions effective to transfer at least some of the at least one oxygenate from the water-depleted hydrogen stream to the second washing fluid.

The first washing fluid is normally a liquid at the temperature employed in the first purification zone, which temperature is typically in the range of about 40° C. to about 160° C. Suitable materials for the first washing fluid include oxygenates, such as $C_1$ to $C_{12}$ alcohols, $C_1$ to $C_{12}$ aldehydes and $C_2$ to $C_{12}$ ketones, especially phenol and/or cyclohexanone, including at least a portion of the liquid effluent from cleavage reaction and/or the dehydrogenation reaction. In various embodiments, the first washing fluid comprises at least 80 wt %, or at least 85 wt %, or at least 90 wt % of a $C_1$ to $C_{12}$ alcohol, a $C_1$ to $C_{12}$ aldehyde, and a $C_2$ to $C_{12}$ ketone. The first washing fluid may also contain minor amounts (less than 10 wt %) of C12+ oxygenate and light hydrocarbon impurities.

The second washing fluid is normally a liquid at the temperature employed in the second purification zone, which temperature is typically in the range of about 40° C. to about 120° C. Suitable materials for the second washing fluid include hydrocarbons, such as $C_4$ to $C_{15}$ hydrocarbons, including both aliphatic and aromatic hydrocarbons, especially benzene and cyclohexane. A suitable source of benzene washing fluid is unreacted benzene from the hydroalkylation reaction, or benzene produced as a by-product in the cyclohexanone dehydrogenation reaction. In one embodiment, the second washing fluid comprises at least 50 wt % of benzene or cyclohexane, or at least 60 wt %, or at least 70 wt %, based upon total weight of the fluid. In some cases, the second washing fluid may also contain minor amounts (less than 40 wt %) of $C_4$ to $C_6$ aliphatic, cyclic and olefinic hydrocarbons and trace amounts of $C_1$ to $C_3$ hydrocarbons, CO and $CO_2$. In one embodiment, the first and/or second washing fluids are obtained from another step in the process to produce phenol and/or cyclohexanone and recycled to purify the hydrogen stream.

In various embodiments, the first washing fluid and second washing fluid each comprise less than 10 wppm of water, or less than 5 wppm or less than 3 wppm.

In various embodiments, the hydrogen stream and the water-depleted hydrogen stream are gases and the first washing fluid and the second washing fluid are liquids.

The first and second purification zones may be located in different vessels but are more preferably located in separate parts of a single vessel. In one embodiment, the first and second purification zones are provided in lower and upper parts respectively of a single, generally vertically oriented purification column. In any event, the different purification zones are arranged so that flow of the second washing fluid into the first purification zone is completely or substantially prevented because the presence of hydrocarbons in the first washing fluid significantly impairs its ability to absorb water from the hydrogen stream.

Although the hydrogen and first and second washing fluids can undergo concurrent and/or countercurrent flow through their respective purification zones, countercurrent flow is preferred. In one embodiment, the hydrogen stream flows in a countercurrent manner to the first washing fluid in the first purification zone, and the water-depleted hydrogen stream flows in a countercurrent manner to the second washing fluid in the second purification zone.

Figure 1:
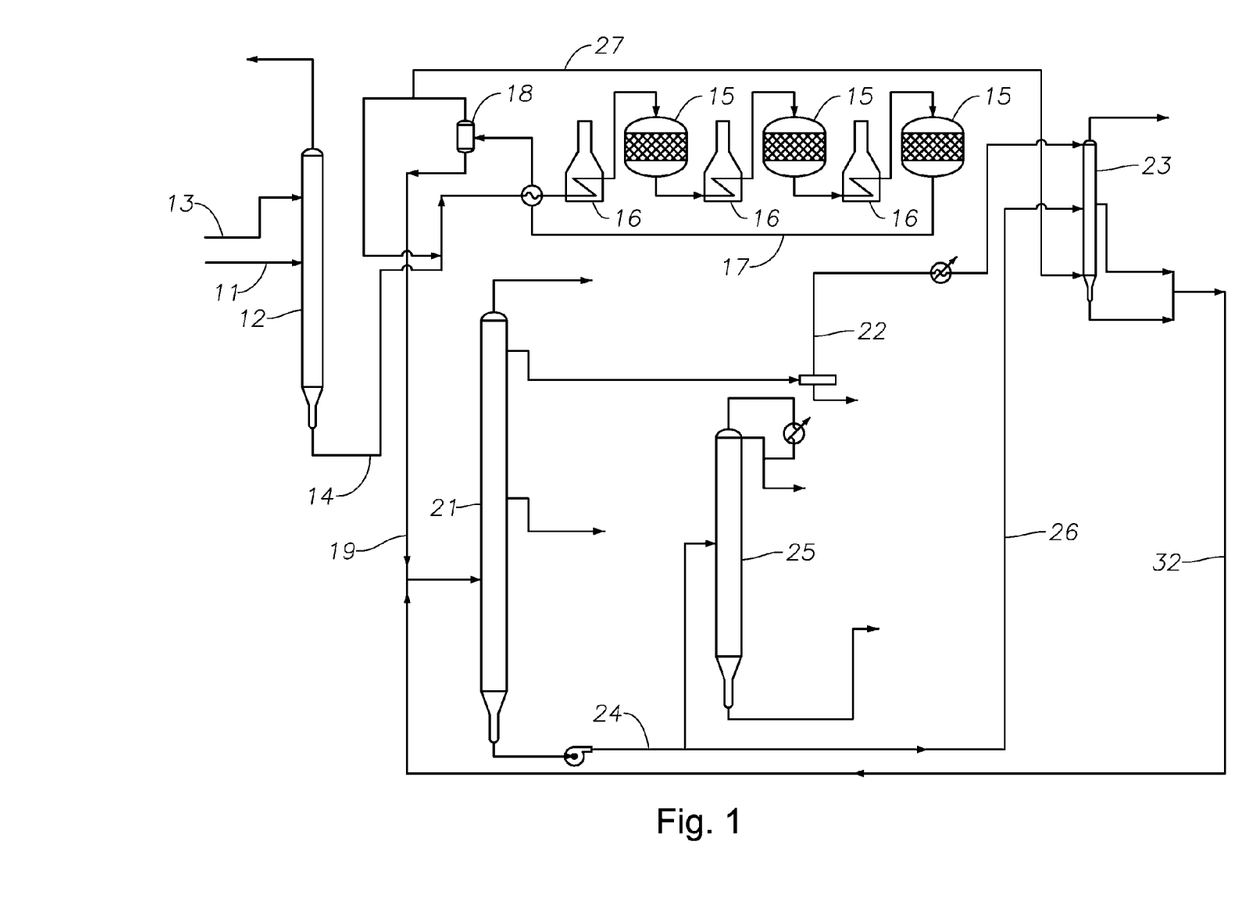
FIG. 1 is a flow diagram of a cyclohexanone dehydrogenation process according to one example of the invention.

In a description of the invention according to FIG. 1, a wet cyclohexanone-containing stream separated from the effluent from a cyclohexylbenzene hydroperoxide cleavage reactor (not shown) is fed via line 11 to a first fractionation column 12. A hydrocarbon, which is liquid at operational temperatures and is heavy enough to condense $C_4+$ components in the cyclohexanone-containing stream, may also be fed to the column 12, via line 13, to assist in separation of the water from the cyclohexanone. Generally, the hydrocarbon comprises unreacted benzene from the benzene hydroalkylation reactor used to produce the cyclohexylbenzene.

The liquid bottoms from the first fractionation column 12, composed mainly of substantially water-free cyclohexanone, is fed by line 14 to a plurality of series-connected dehydrogenation reactors 15, each having a preheater 16. In the dehydrogenation reactors 15, the cyclohexanone is converted mainly to phenol and hydrogen, together with some benzene and water. The effluent from the final dehydrogenation reactor 15 is fed by line 17 to a condenser 18, where the effluent is divided into a liquid stream containing phenol and benzene and a gaseous hydrogen stream containing water and some $C_6$ oxygenate impurities. The liquid stream is supplied by line 19 to a second fractionation column 21, where a benzene-rich stream is removed as overhead and supplied by line 22 to the top of a purification column 23. The major portion of the phenol-containing bottoms stream from the second fractionation column 21 is supplied by line 24 to a third fractionation column 25, where heavies are removed before the phenol-rich stream is recovered for further treatment. In addition, part of the bottoms from second fractionation column 21 is supplied by line 26 to a central portion of the purification column 23. The gaseous hydrogen stream from the condenser 18 is compressed and supplied by line 27 to the bottom of the purification column 23.

Figure 2:
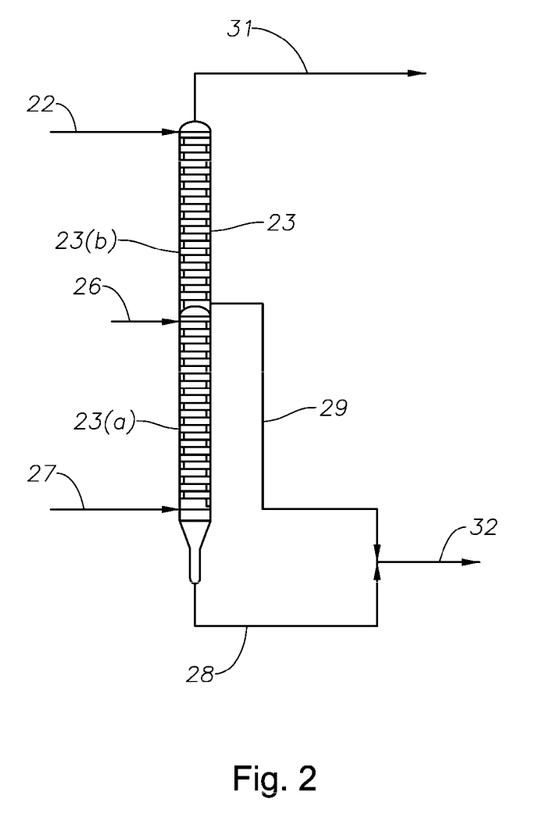
FIG. 2 is an enlarged view of the hydrogen purification stage of the process illustrated in FIG. 1.

The purification column 23 is shown in more detail in FIG. 2 and includes a lower purification zone 23(a) and an upper purification zone 23(b). The gaseous hydrogen stream (containing water) is supplied by line 27 to the bottom of the lower purification zone 23(a), whereas the phenol-containing bottoms stream from the second fractionation column 21 is supplied via line 26 to the top of the lower purification zone 23(a). The hydrogen and phenol-containing stream flow in countercurrent fashion through the lower purification zone 23(a) such that water is transferred from the hydrogen stream to the phenol-containing stream and exits the zone 23(a) through line 28.

After passage through the lower purification zone 23(a), the hydrogen flows into the upper purification zone 23(b) where it flows in countercurrent fashion to the benzene-rich stream from the second fractionation column 21 which is fed by line 22 to the top of the zone 23(b). Oxygenates are transferred from the hydrogen stream to the benzene-rich and exit the bottom of the upper purification zone 23(b) through line 29. A dry hydrogen stream that has a reduced amount of $C_6$ oxygenates exits the top of the purification zone 23(b) through line 31 and can be recycled to a benzene hydroalkylation reactor (not shown). The water-containing phenol stream from line 28 and the oxygenate-containing benzene stream from line 29 can be combined and fed by line 32 to the second fractionation column 21.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for purifying a hydrogen stream comprising water, the process comprising:
    (a) contacting the hydrogen stream in a first purification zone with a first washing fluid under conditions effective to transfer at least some of the water from the hydrogen stream to the first washing fluid, thereby transforming the hydrogen stream into a water-depleted hydrogen stream,
    wherein the water-depleted hydrogen stream further comprises at least one oxygenate;
    (b) transferring at least a portion of the water-depleted hydrogen stream from the first purification zone to a second purification zone; and
    (c) contacting at least a portion of the water-depleted hydrogen stream with a second washing fluid comprising at least one hydrocarbon in the second purification zone under conditions effective to transfer at least some of the at least one oxygenate from the water-depleted hydrogen stream to the second washing fluid.

2. The process of claim 1, wherein the hydrogen stream and the water-depleted hydrogen stream are gases and the first washing fluid and the second washing fluid are liquids.

3. The process of claim 1, wherein the hydrogen stream contains at least 2 wt % of hydrogen, based upon total weight of the stream.

4. The process of claim 1, wherein the hydrogen stream flows in a countercurrent manner to the first washing fluid in the first purification zone, and the water-depleted hydrogen stream flows in a countercurrent manner to the second washing fluid in the second purification zone.

5. The process of claim 1, wherein the at least one oxygenate is supplied to the water-depleted hydrogen stream from at least one of: (i) the hydrogen stream; and (ii) the first washing fluid.

6. The process of claim 1, wherein the at least one oxygenate is a C6 oxygenate.

7. The process of claim 1, wherein the at least one oxygenate is phenol.

8. The process of claim 1, wherein the first washing fluid comprises at least 80 wt % of an oxygenate selected from a C1 to C12 alcohol, a C1 to C12 aldehyde and a C2 to C12 ketone.

9. The process of claim 1, wherein the first washing fluid comprises at least one of phenol and cyclohexanone.

10. The process of claim 1, wherein the second washing fluid comprises at least one of benzene and cyclohexane.

11. The process of claim 1, wherein the second washing fluid comprises at least 50 wt % of benzene or cyclohexane.

12. The process of claim 1, wherein the first washing fluid and the second washing fluid each comprise less than 10 wppm of water.

13. The process of claim 1, wherein the first purification zone and the second purification zone are provided in separate sections of a single purification column arranged such that the second washing fluid does not enter the first purification zone.

14. The process of claim 1, and further comprising:
    (d) contacting cyclohexanone with a dehydrogenation catalyst under dehydrogenation conditions effective to convert at least a portion of the cyclohexanone into phenol and produce a dehydrogenation effluent comprising phenol, hydrogen and water;
    (e) separating the dehydrogenation effluent into at least a phenol-rich stream and a hydrogen-rich stream, wherein the hydrogen-rich stream comprises at least phenol and water impurities; and
    (f) supplying the hydrogen-rich stream to the contacting (a) as the hydrogen stream.

15. The process of claim 14, wherein the dehydrogenation conditions include a temperature of about 250° C. to about 500° C.

16. A process for producing phenol, the process comprising:
(a) reacting benzene and hydrogen in the presence of a hydroalkylation catalyst to form cyclohexylbenzene;
(b) oxidizing at least a portion of the cyclohexylbenzene to form cyclohexylbenzene hydroperoxide;
(c) cleaving at least a portion of the cyclohexylbenzene hydroperoxide to form phenol and cyclohexanone;
(d) dehydrogenating at least a portion of the cyclohexanone in the presence of a dehydrogenation catalyst to form a dehydrogenation effluent comprising phenol, hydrogen and water;
(e) separating the dehydrogenation effluent into at least a phenol-rich stream and a hydrogen-rich stream, wherein the hydrogen-rich stream comprises at least phenol and water;
(f) contacting at least a portion of the hydrogen-rich stream in a first purification zone with a first washing fluid under conditions effective to transfer at least a portion of the water from the hydrogen-rich stream to the first washing fluid, thereby forming a water-depleted hydrogen-rich stream;
(g) transferring at least a portion of the water-depleted hydrogen-rich stream from the first purification zone to a second purification zone; and
(h) contacting at least a portion of the water-depleted hydrogen-rich stream with a second washing fluid comprising at least one hydrocarbon in the second purification zone under conditions effective to transfer at least a portion of the phenol from the hydrogen-rich stream to the second washing fluid to form an oxygenate-depleted hydrogen stream, wherein the hydrogen stream and the water-depleted hydrogen stream are gases and the first and second washing fluids are liquids.

17. The process of claim 16, further comprising:
(i) recycling at least a portion of the oxygenate-depleted hydrogen stream from (h) to the reacting step (a).

18. The process of claim 16, wherein the phenol-rich stream comprises water and the process further comprises: (i) removing at least some of the water from the phenol-rich stream to form a water-depleted phenol-rich stream; and (ii) using the water-depleted phenol-rich stream as the first washing fluid.

19. The process of claim 16, wherein the dehydrogenation catalyst comprises: (i) a support; (ii) a dehydrogenation component comprising at least one metal or compound thereof selected from Groups 6 to 10 of the Periodic Table of Elements; and (iii) tin or a tin compound, wherein the tin is present in an amount of 0.01 to about 0.25 wt %, the wt % based upon the total weight of the catalyst composition.

20. The process of claim 16, wherein the hydrogen-rich stream flows in a countercurrent manner to the first washing fluid in the first purification zone, and the water-depleted hydrogen-rich stream flows in a countercurrent manner to the second washing fluid in the second purification zone.

21. The process of claim 16, wherein the first washing fluid comprises an oxygenate.

22. The process of claim 16, wherein the first washing fluid comprises at least one of phenol and cyclohexanone.

23. The process of claim 16, wherein the first washing fluid comprises at least a portion of the phenol and cyclohexanone produced by the cleaving (c).

24. The process of claim 16, wherein the first purification zone and the second purification zone are provided in separate sections of a single purification column arranged such that the second washing fluid does not enter the first purification zone.

* * * * *